(12) United States Patent
Hermans et al.

(10) Patent No.: US 11,680,030 B2
(45) Date of Patent: Jun. 20, 2023

(54) GAS PHASE OZONE-MEDIATED SELECTIVE OXIDATIVE DEHYDROGENATION OF ALKANES

(71) Applicant: WISCONSIN ALUMNI RESEARCH FOUNDATION, Madison, WI (US)

(72) Inventors: Ive Hermans, Middleton, WI (US); William McDermott, Madison, WI (US); Edgard Lebron Rodriguez, Madison, WI (US); Unni Ravi Kurumbail, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/720,081

(22) Filed: Apr. 13, 2022

(65) Prior Publication Data
US 2022/0332666 A1   Oct. 20, 2022

Related U.S. Application Data

(60) Provisional application No. 63/174,109, filed on Apr. 13, 2021.

(51) Int. Cl.
*C07C 5/48* (2006.01)

(52) U.S. Cl.
CPC ...................... *C07C 5/48* (2013.01)

(58) Field of Classification Search
CPC ........................................ C07C 5/48
See application file for complete search history.

(56) References Cited

U.S. PATENT DOCUMENTS

| 5,386,074 A * | 1/1995 | Durante ............. C07C 2/82 585/629 |
| 10,011,540 B2 | 7/2018 | Hermans et al. |
| 10,125,059 B2 | 11/2018 | Hermans et al. |
| 10,407,364 B2 | 11/2019 | Hermans et al. |

* cited by examiner

*Primary Examiner* — Thuan D Dang
(74) *Attorney, Agent, or Firm* — Quarles & Brady LLP

(57) ABSTRACT

Improved methods of oxidative dehydrogenation (ODH) of alkanes and alkylbenzenes to the corresponding olefins are disclosed. The disclosed methods use ozone ($O_3$) to mediate the oxidative dehydrogenation reaction with high selectivity for the desired product, and no heterogeneous ODH catalyst is needed.

15 Claims, 13 Drawing Sheets

GAS PHASE OZONE-MEDIATED SELECTIVE OXIDATIVE DEHYDROGENATION OF ALKANES

CROSS-REFERENCE TO RELATED APPLICATIONS

This application claims benefit of priority to U.S. Provisional Application 63/174,109, filed Apr. 13, 2021, the contents of which is incorporated by reference in its entirety.

STATEMENT REGARDING FEDERALLY SPONSORED RESEARCH

This invention was made with government support under DE-SC0017918 awarded by the US Department of Energy. The government has certain rights in the invention.

FIELD OF THE INVENTION

The disclosure relates to compositions and methods for using ozone ($O_3$) to mediate the oxidative dehydrogenation of alkanes and alkylbenzenes.

BACKGROUND OF THE INVENTION

The production of light olefins is a cornerstone of the modern chemical industry, as they serve as the building block of a myriad of polymers, oxygenates, and bulk chemical intermediates. Light olefins have traditionally been produced through the steam cracking of naphtha, but the abundance of natural gas obtained from shale deposit has driven a major shift from naphtha to ethane as a cracking feedstock. As ethane cracking produces primarily ethylene rather than a wide range of olefins as obtained through naphtha cracking, a gap has emerged between the supply of propylene and other non-ethylene light olefins from steam crackers and their demand from the chemical industry.

To fill this gap, on-purpose processes like propane dehydrogenation (PDH) have been developed. These and other on-purpose dehydrogenation technologies are energy intensive, because the dehydrogenation reaction is highly endothermic. Furthermore, because they require high temperature conditions, they result in substantial catalyst deactivation due to the formation of coke on the catalyst surface. Thus, they require continuous catalyst regeneration. In addition, these processes may require substantially reduced pressure to shift the dehydrogenation equilibrium towards the desired products, further contributing to the high production costs associated with these methods. Accordingly, other processes are required to provide the chemical industry with a more efficient route to produce propylene and other light olefins.

Oxidative dehydrogenation (ODH), the catalytic dehydrogenation of feedstock light alkanes in the presence of oxygen, is an alternative to conventional dehydrogenation that addresses each of the disadvantages of current DH technology. When oxygen is co-fed to act as a reactant, the reaction thermodynamics are altered such that the resulting net reaction is exothermic. Accordingly, the reaction can proceed at much lower reaction temperatures, resulting in decreased energy costs and increased catalyst stability. Oxygen in the feed stream also eliminates coke formation on the catalyst surface and thus creates reduced need for catalyst regeneration.

Despite these purported advantages, industrial-scale ODH processes have not been implemented, due to poor control of unwanted side-reactions (mainly the over-oxidation of olefin to CO and $CO_2$), which results in low olefin selectivity at conversions necessary for industrial implementation. For example, typical catalysts for propane ODH typically provide ~50-60% selectivity to propene at 10% propane conversion, with the byproducts largely made up of CO and $CO_2$. As a result, even after more than 30 years of research into catalysis development for ODH (almost entirely focused on supporting vanadium oxide on amorphous oxide supports (e.g., $SiO_2$, $Al_2O_3$, $TiO_2$, $CeO_2$, $ZrO_2$) and structured oxides (e.g., MCM-41, SBA-15)), ODH has not been successfully used in the industrial-scale production of $C_3$ and $C_4$ olefins.

In recent years, Iye Hermans et al. have disclosed the use of various boron-containing materials as high performing catalysts for the ODH of alkanes (see, e.g., U.S. Pat. Nos. 10,011,540; 10,125,059 and 10,407,364). More specifically, bulk boron materials, such as hexagonal boron nitride (hBN), exhibit high selectivity towards propylene, and are currently recognized as the benchmark catalyst for the ODH of propane. However, such materials are expensive to synthesize, making them unlikely candidates for large-scale, industrial applications.

Accordingly, there is a need in the art for improved methods for the oxidative dehydrogenation of light alkanes and alkylbenzenes to the corresponding light olefins and alkenyl benzenes that exhibit the improved selectivity of using bulk boron materials as catalysts, while potentially being simpler and less expensive to implement in large-scale industrial settings.

BRIEF SUMMARY OF THE INVENTION

Disclosed herein are new and improved compositions and methods for facilitating the oxidative dehydrogenation of alkanes and alkylbenzenes to the corresponding olefins and alkenylbenzenes. The improved methods use ozone ($O_3$) to mediate the ODH reaction. The ozone may be generated and added to the reaction stream on-site, with no need for a separate catalyst. Although this method is simpler, potentially more efficient, and less expensive than previously disclosed catalyst-based ODH processes, selectivity for the desired olefin reaction product is very high, comparable to that exhibited by hBN catalysts.

Accordingly, this disclosure encompasses a method of making one or more desired chemical products. The method includes the step of contacting one or more liquid or gaseous reactants with oxygen ($O_2$) and ozone ($O_3$), where the ozone mediates the oxidative dehydrogenation (ODH) of the one or more liquid or gaseous reactants to form the one or more desired chemical products, wherein the one or more liquid or gaseous reactants comprises an alkane or a hydrocarbon comprising an alkyl group and the desired chemical products comprise one or more olefins or one or more hydrocarbons comprising an alkenyl group.

In some embodiments, the one or more liquid or gaseous reactants are selected from a $C_2$-$C_5$ n-alkane, a $C_3$-$C_5$ iso-alkane, a $C_2$-$C_5$ alkylbenzene, and any combination thereof. In some such embodiments, the one or more liquid or gaseous reactants comprises propane and the desired chemical product is propene. In some embodiments, the one or more liquid or gaseous reactants comprises butane and the desired chemical product comprises 1-butene, 2-butene, isobutene, butadiene, or any combination thereof. In some such embodiments, the one or more liquid or gaseous reactants comprises ethylbenzene and the desired chemical product is styrene.

In some embodiments, the contacting step occurs in the absence of a heterogeneous ODH catalyst or a catalytically active surface.

In some embodiments, the one or more liquid or gaseous reactants, the oxygen, and the ozone are introduced into the reactor chamber together. In other embodiments, the one or more liquid or gaseous reactants, the oxygen, and the ozone are introduced into the reactor chamber separately.

In some embodiments, the reactor chamber comprises one or more inlets dispersed along the chamber to introduce the oxygen or the ozone into a reaction path for a propagating reactant stream of the one or more liquid or gaseous reactants through the reactor chamber.

In some embodiments, the reactor chamber does not include a heterogeneous ODH catalyst or a catalytically active surface.

In some embodiments, the method exhibits greater than 70% selectivity for the one or more desired chemical products. In some such embodiments, the method exhibits greater than 75% selectivity for the one or more desired chemical products. In some such embodiments, the method exhibits greater than 80% selectivity for the one or more desired chemical products.

In a second aspect, the disclosure encompasses a system for making one or more desired chemical products. In some embodiments, the system comprises (a) a reactor chamber comprising one or more inlets for introducing one or more liquid or gaseous reactants, oxygen ($O_2$); and ozone ($O_3$) into the reactor chamber; (b) an ozone generator in fluid communication with the reactor chamber and configured to introduce the ozone into the reactor chamber; (c) a reactant source in fluid communication with the reactor chamber and configured to introduce the one or more liquid or gaseous reactants into the reactor chamber, wherein the one or more liquid or gaseous reactants comprises an alkane or a hydrocarbon comprising an alkyl group; (d) an oxygen source in fluid communication with the reactor chamber and configured to introduce oxygen into the reactor chamber; (e) an optional diluent source in fluid communication with the reactor chamber and configured to introduce a diluent into the reactor chamber; and (f) a heating element for heating the one or more liquid or gaseous reactants, the oxygen; the ozone, and, if present, diluent within the reactor chamber to a temperature where the ozone mediates the oxidative dehydrogenation (ODH) of the one or more liquid or gaseous reactants to form the one or more desired chemical products, wherein the desired chemical products comprise one or more olefins or one or more hydrocarbons comprising an alkenyl group.

Further features and advantages of the disclosed methods and systems will be apparent from the following detailed description when taken in conjunction with the accompanying drawings.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
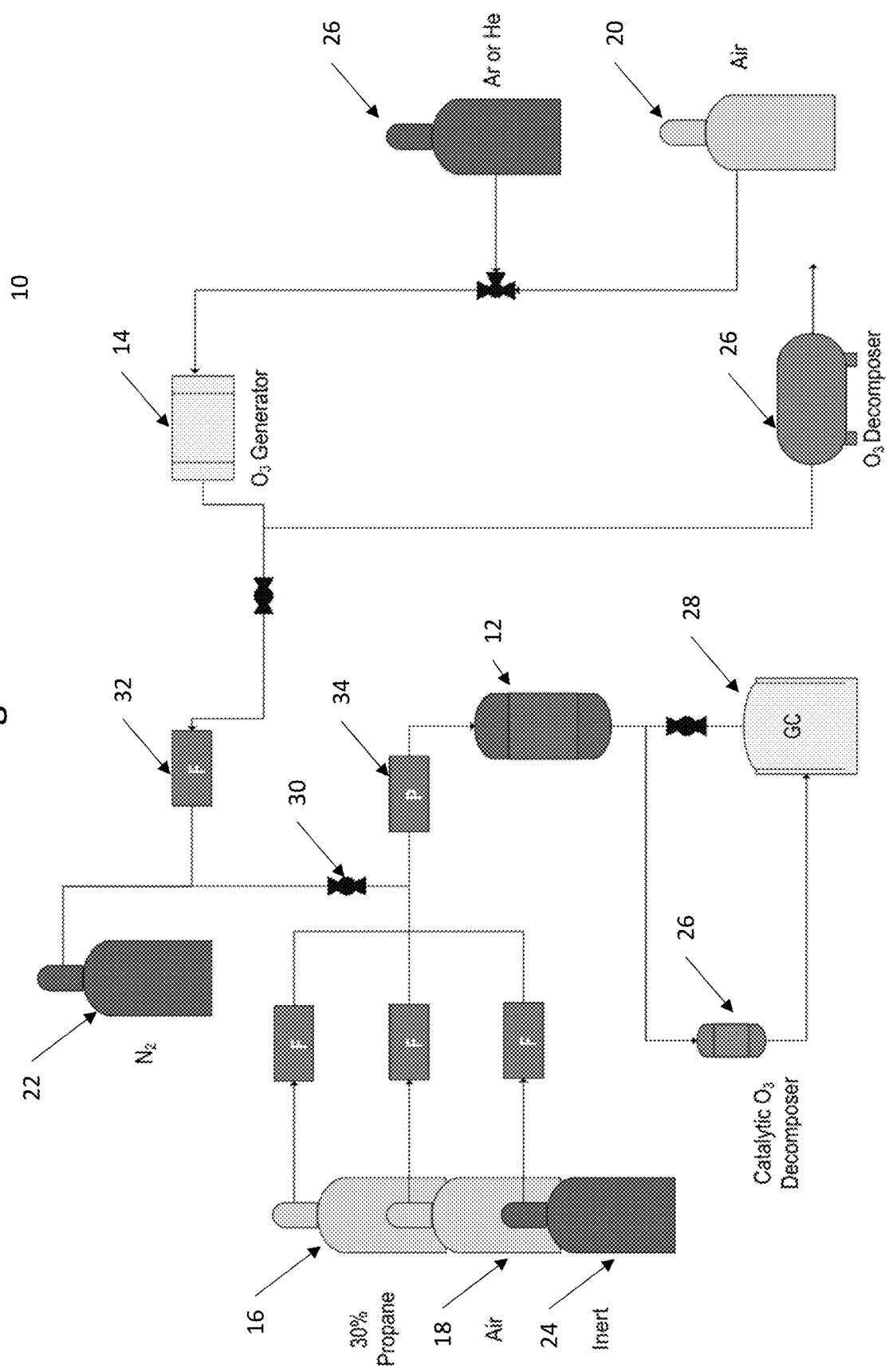
FIG. 1 is a schematic diagram illustrating an exemplary experimental setup for generating $O_3$ and for demonstrating the successful use of the generated $O_3$ to mediate the oxidative dehydrogenation of propane (ODHP).

This disclosure is based on the discovery that the use of an ozone mediator facilitates improved oxidative dehydrogenation of alkanes to desired olefins, such as propane to propylene, or oxidative dehydrogenation of alkylbenzenes to desired alkenyl benzenes, such as ethyl benzene to styrene.

The disclosed methods exhibit high selectivity towards the desired product while decreasing the production of unwanted byproducts, such as CO and $CO_2$. Furthermore, the process can occur at relatively low temperatures, and no additional ODH catalyst is needed, thus avoiding the expense and complications of catalyst production, maintenance, and regeneration.

Currently, the chemical industry produces light alkenes, such as propylene, through two main routes: the cracking of petroleum-derived feedstocks or the non-oxidative dehydrogenation (DH) of propane to propylene. DH has significant drawbacks, including high reaction temperatures and catalyst deactivation from carbon deposition. An alternative to non-oxidative dehydrogenation is the oxidative dehydrogenation, which incorporates oxygen into a feed of an alkane to lower the temperature required to produce alkenes over a catalyst and to prevent catalyst coking.

Prior studies established that the mechanism of propane transformation over hBN is a surface-initiated gas phase reaction, where hydrogen abstraction at the surface is followed by alkyl radical reaction with oxygen in the gas phase that leads to selective ODH. Use of hBN has been established to provide new 80% propylene selectivity at 15% conversion of propane.

Here, instead of using a catalyst surface to initiate selective ODH, the Examples demonstrate that ozone in the absence of any other ODH catalyst may be used. Moreover, the Examples demonstrate that this route is just as selective as hBN in the production of propylene and can be performed at lower temperatures than typically required for ODH over hBN.

Because ozone-mediated ODH of light alkanes to the corresponding alkene (e.g., propane to propylene) does not require a separate catalyst material, it therefore limits concerns of catalyst deactivation and removes the cost of catalyst development, scale-up, and replacement. Additionally, lower reaction temperatures (in a non-limiting example, 425-475° C. versus 475-525° C. for hBN-catalyzed ODH with a similar product distribution) reduce the energy required to selectively produce the desired product.

Many companies are looking toward electricity to heat their reactors rather than fuel burning furnaces. In the disclosed methods, ozone could be produced through the flow of air through an electrical discharge, which supports the increased electrification strategy of the chemical industry.

Although other researchers have shown that gas-phase mediated production of propylene can be mediated by oxides of nitrogen, this method leads to the production of nitric acid, which would be a huge hurdle in scale-up. Additionally, they use conditions that are not ideal for commercial applications (small propane concentrations with mixtures of oxygen and inert that are unlike air). In contrast, we demonstrate in this application that we can use mixtures of oxygen/nitrogen close to air as our oxidant, which would make intense air purification unnecessary, thus further reducing cost.

In a non-limiting example, a plant could be constructed centered around ozone-mediated production of propylene, just as they are currently constructed for DH or envisioned for ODH. However, these plants would differ as this would be a non-catalytic process, and techniques required for usage of a catalysts would not be required. Unlike plants that typically require burning fuel for heating, this plant could be completely powered by electricity for both heating purposes and ozone-producing purposes. This would potentially result in a lower carbon footprint overall. Ideally, the electricity used would be produced through wind energy or hydroelectric means.

Definitions

As used herein, the term "oxidative dehydrogenation" refers to an oxidative process of dehydrogenating hydrocarbons (e.g. alkanes and hydrocarbons comprising an alkyl group) to corresponding olefinic counterparts in the presence of oxygen.

As used herein, the term "hydrocarbon" refers to an organic compound containing only hydrogen and carbon atoms. In some embodiments, the catalytic material is capable of catalyzing oxidative dehydrogenation (ODH) of an alkane or an alkyl group.

As used herein, the term "alkane" refers to saturated hydrocarbons having a formula of $C_nH_{2n+2}$, wherein n is a positive integer greater than or equal to 1. Examples of alkanes include, but are not limited to methane, ethane, n-propane, iso-propane, butane, etc.

As used herein, the term "alkyl" refers to a saturated, straight or branched hydrocarbon chain radical. In some embodiment, the number of carbon atoms in an alkane or alkyl moiety is indicated by the prefix "$C_x$-$C_y$", wherein x is the minimum and y is the maximum number of carbon atoms in the substituent. Representative examples of an alkyl include, but are not limited to, methyl, ethyl, n-propyl, iso-propyl, n-butyl, sec-butyl, iso-butyl, tert-butyl, n-pentyl, isopentyl, neopentyl, etc.

As used herein, the term "olefin" refers to an unsaturated hydrocarbon containing at least one "C=C" double bond.

The term "alkenyl" as used herein, refers to a straight or branched hydrocarbon chain containing at least one carbon-carbon double bond. Non-limiting examples of alkenyl include buta-1,3-dienyl, ethenyl, 2-propenyl, 2-methyl-2-propenyl, 3-butenyl, 4-pentenyl, 5-hexenyl, etc.

As used herein, the term "alkylbenzene" refers to benzene attached to at least one alkyl group as described herein. Non-limiting examples of alkylbenzene refers to methylbenzene, ethylbenzene, propylbenzene, and the like. In some embodiments, the one or more liquid or gaseous reactants comprise an alkylbenzene, such as ethylbenzene.

As used herein, the term "diluent" refers to one or more chemically inert or inactive liquids and gases. A diluent may be selected to serve one or more different purposes. One use of the diluent is to dilute the feed to keep the reaction out of the flammable regime. Another use of the diluent is to serve as a heat transfer medium based on its heat capacity. Yet another use of the diluent is to shift the product distribution. Thus, diluents may be selected to achieve a desired level of conversion and/or product selectivity. Diluent and inert gas can be used interchangeably in appropriate circumstances. Common diluents include but are not limited to nitrogen ($N_2$), water ($H_2O$), methane ($CH_4$), carbon dioxide ($CO_2$), argon (Ar), helium (He), and any combination thereof. In some embodiments, the diluent comprises nitrogen. In some embodiments, the diluent comprises water. In some embodiments, the diluent comprises methane. In some embodiments, the diluent comprises nitrogen and water, nitrogen and methane, or water and methane.

As used herein, the term "heterogeneous ODH catalyst" refers to catalysts of which the phase differs from that of the reactants or products. Common heterogeneous ODH catalysts are composed of metals or non-metals including but are not limited to boron, vanadium, nickel, chromium, manganese, aluminum, gold, and molybdenum.

As used herein, the term "catalytically active surface" refers to a surface composed of catalytically active sites capable of accelerating the oxidative dehydrogenation reactions.

Exemplary Ozone Concentrations

In a non-limiting example, the method can be performed using ozone concentrations less than or equal to about 1000 ppm. The Examples demonstrate increased activity using higher ozone concentrations, but optimal selectivity for the desired product (e.g., propylene) is obtained at lower ozone concentrations. Thus, ozone concentration can be varied to obtain the desired combination of activity and selectivity.

In some embodiments, ozone may be introduced into a reactor chamber via one or more inlets. Ozone may be introduced into the reactor chamber with the liquid or gaseous reactants via the same inlet or without the liquid or gaseous reactants via a different inlet than the one that introduces the liquid or gaseous reactants. In some embodiments, ozone is introduced into the reactor chamber via two or more different inlets. When ozone is introduced via two or more inlets, the local concentration of ozone at the inlet may be selected to improve selectivity while increasing the activity of ozone throughout the reactor chamber as a whole.

In some non-limiting exemplary embodiments, the ozone concentration used is 0.01 to 1000 ppm. In some such embodiments, the ozone concentration used is within a range that (A) has a minimum concentration of 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 720, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, or 995 ppm $O_3$; and (B) has a maximum concentration of 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 720, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 ppm $O_3$. In some embodiments, the ozone is introduced into the reactor chamber at a concentration of 1-50 ppm, 51-100 ppm, 101-150 ppm, 151-200 ppm, 201-250 ppm, 251-300 ppm, 301-350 ppm, 351-400 ppm, 401-450 ppm, 451-500 ppm, 501-550 ppm, 551-600 ppm, 601-650 ppm, 651-700 ppm, 701-750 ppm, 751-800 ppm, 801-850 ppm, 851-900 ppm, 901-950 ppm, or 951-1000 ppm.

In other non-limiting exemplary embodiments, the ozone concentration used is greater than 1000 ppm. In some such embodiments, the ozone concentration used is within a range that (A) has a minimum concentration of 1000, 1500, 2000, 2500, 3000, 3500, 4000, 4500, 5000, 5500, 6000, 6500, 7000, 7500, 8000, 8500, 9000, or 9500 ppm $O_3$; and (B) has a maximum concentration of 1500, 2000, 2500, 3000, 3500, 4000, 4500, 5000, 5500, 6000, 6500, 7000, 7500, 8000, 8500, 9000, 9500, or 10000 ppm $O_3$. In some such embodiments, other reaction conditions may be adjusted to increase selectivity towards the desired product.

Exemplary Oxygen Concentrations

In a non-limiting example, the method can be performed using oxygen concentrations less than or equal to about 25% $O_2$ by volume. In some embodiments, the oxygen is introduced at a concentration substantially similar to air. Accordingly, air may be used as the oxygen source. The Examples demonstrate increased activity using higher oxygen concentrations, but optimal selectivity for the desired product (e.g., propylene) is obtained at lower oxygen concentrations. Thus, like ozone, oxygen concentration can be varied to obtain the desired combination of activity and selectivity.

In some embodiments, the oxygen concentration used is 1 to 25% $O_2$ by volume. In some such embodiments, the oxygen concentration used is within a range that (A) has a minimum concentration of 1, 2, 3, 4, 5, 5, 7, 8, 9, 10, 11, 12, 13, 14, 15, 16, 17, 18, 19, 20, 21, 22, 23, or 24% $O_2$ by volume; and (B) has a maximum concentration of 2, 3, 4, 5, 5, 7, 8, 9, 10, 11, 12, 13, 14, 15, 16, 17, 18, 19, 20, 21, 22, 23, 24, or 25% $O_2$ by volume. In some such embodiments, the oxygen is introduced into the reactor chamber at a concentration of 1.0-5.0%, 5.1-10.0%, 10.1-15.0%, 15.1-20.0%, or 20.1-25.0% by volume.

Exemplary Reactant Concentrations

In a non-limiting example, the method can be performed using one or more liquid or gaseous reactants at concentrations less than or equal to about 50% by volume. The concentration of the one or more liquid or gaseous reactants can be varied to obtain the desired combination of activity and selectivity.

In some embodiments, the one or more liquid or gaseous reactants concentration used is 5 to 50% by volume. In some such embodiments, the concentration used is within a range that (A) has a minimum concentration of 5, 10, 15, 20, 25, 30, 35, 40, or 45% by volume; and (B) has a maximum concentration of 10, 15, 20, 25, 30, 35, 40, 45, or 50 $O_2$ by volume. In some embodiments, the one or more liquid or gaseous reactants is introduced into the reactor chamber at a concentration of 5.0-10.0%, 10.0-15.0%, 15.0-20.0%, 25.0-30.0%, 30.0-35.0, 35.0-40.0, or 45.0-50.0% by volume.

Exemplary Diluent Concentrations

In a non-limiting example, the method can be performed using diluent concentrations less than or equal to about 70% by volume. In some embodiments, the diluent is introduced at a concentration substantially similar to $N_2$ in air. Accordingly, air may be used as the diluent source. In some embodiments, the diluent comprises $N_2$. The diluent concentration can be varied to obtain the desired combination of activity and selectivity.

In some embodiments, the diluent concentration used is 0.01 to 70% diluent by volume. In some embodiments, the diluent concentration used is within a range that (A) has a minimum concentration of 1, 10, 20, 30, 40, 50, or 60% diluent by volume; and (B) has a maximum concentration of 10, 20, 30, 40, 50, 60, or 70% diluent by volume. In some embodiments, the diluent is introduced into the reactor chamber at a concentration of 1.0-10.0%, 10.0-20.0%, 20.0-30.0%, 30.0-40.0%, 40.0-50.0, 50.0-60.0, or 60.0-70.0% by volume.

Exemplary Reaction Temperature

In a non-limiting example, the method can be performed at a temperature from about 400° C. to 800° C. The temperature can be varied to obtain the desired combination of activity and selectivity.

In some embodiments, the temperature is within a range that (A) has a minimum temperature of 400, 425, 450, 475, 500, 525, 550, 575, 600, 625, 650, 675, 700, 725, 750, or 775° C.; and (B) has a maximum temperature of 425, 450, 475, 500, 525, 550, 575, 600, 625, 650, 675, 700, 725, 750, 775, or 800° C. In some such embodiments, the temperature within the reactor chamber is from 400° C. to 500° C. In some such embodiments, the temperature within the reactor chamber is from 400° C. to 475° C. In some such embodiments, the temperature within the reactor chamber is from 400° C. to 450° C.

Systems for Performing Ozone-Mediated ODH

Another aspect of the invention provides for systems for performing the methods disclosed herein. FIG. 1 illustrates an exemplary system for performing ozone-mediated ODH. The system 10 comprises a reactor chamber 12 comprising one or more inlets for introducing one or more liquid or gaseous reactants, oxygen ($O_2$); and ozone ($O_3$) into the reactor chamber. The system may comprise one or more valves or regulators for controlling the concentration of the one or more liquid or gaseous reactions, oxygen, ozone, and optional diluents introduced into the reaction chamber 12 in accord with the methods described herein.

FIG. 1 illustrates that the one or more liquid or gaseous reactants, oxygen ($O_2$); and ozone ($O_3$) into the reactor chamber 12 are introduced together. In other embodiments, the one or more liquid or gaseous reactants, oxygen ($O_2$); and ozone ($O_3$) into the reactor chamber 12 via two or more different inlets. In some embodiments, the reactor chamber comprises one or more inlets dispersed along the chamber to introduce the oxygen or the ozone into a reaction path for a propagating reactant stream of the one or more liquid or gaseous reactants through the reactor chamber. In some embodiments, ozone is introduced into the reaction chamber by two or more inlets, e.g., 2, 3, 4, 5, 6, 7, 8, 9, 10, or more than 10 inlets.

The system 10 also comprises an ozone generator 14 in fluid communication with the reactor chamber 12 and configured to introduce the ozone into the reactor chamber. The ozone generator 14 is supplied from an oxygen source 20, which in some embodiments is air or substantially pure oxygen (e.g., greater than 95%, 98%, or 99% $O_2$ by volume). Suitably, the ozone generator introduces the ozone into the reactor chamber at a concentration from 0.1 to 1000 ppm.

The system 10 further comprises a reactant source 16 in fluid communication with the reactor chamber 12 and configured to introduce the one or more liquid or gaseous reactants into the reactor chamber. In an exemplary embodiment, the reactant source is configured to introduce 30% propane by volume. In other embodiments, the reactant source may comprise a different alkane, alkylbenzene, or combinations of alkanes and/or alkylbenzenes. Suitably, the reactant source introduces the one or more liquid or gaseous reactants into the reactor chamber at a concentration from 5% to 50% by volume.

The system 10 further comprises an oxygen source 18 in fluid communication with the reactor chamber 12 and configured to introduce oxygen into the reactor chamber. In some embodiments, the oxygen source 20 that introduces oxygen into the ozone generator 14 provides some or all of the oxygen introduced into the reaction chamber 12. Suitably, the oxygen source introduces the oxygen into the reactor chamber 12 at a concentration from 1% to 25% by volume.

The system 10 may optionally comprise one or more diluent sources. As illustrated in FIG. 1, diluents such as $N_2$ from a nitrogen source 22 and inert gases from a tank 24 are added to obtain the desired reactor concentrations. In some embodiments, a diluent, such as Ar or He, may by provided to the ozone generator 14 from a tank 26. Suitably, the diluent source introduces the diluent into the reactor chamber 13 at a concentration from 0.01% to 70% by volume. The system 10 also comprises a heating element (not labeled) for heating the one or more liquid or gaseous reactants, the oxygen; the ozone, and, if present, diluent within the reactor chamber 12 to a temperature where the ozone mediates the oxidative dehydrogenation (ODH). Suitably, heating element heats the ozone, the oxygen, and the one or more liquid or gaseous reactants within the reactor chamber to a temperature from 400° C. to 800° C.

The system 10 may optionally comprise one or more ozone decomposers 26. Ozone contaminated effluent from the reaction chamber 12 passes through the ozone decomposer 26 converts the ozone into molecular oxygen so that it can then be vented if no other contaminants are present.

The system 10 may optionally comprise one or more analytical systems 28, such as a gas chromatograph, integrated into the system to monitor the progress of the ODH such as conversion or selectivity.

Each of the ozone generator 14, reactant source 16, oxygen sources 18 or 20, diluent sources 22, 24 or 26 may optionally comprise one or more valves 30 or regulators 32 for controlling the concentration of the one or more liquid or gaseous reactions, oxygen, ozone, and optional diluents introduced into the reaction chamber 12. In some embodiments, the regulator 32 is a mass flow controller such as those labeled by F in FIG. 1. The system 10 may also comprise one or more pressure gauges 34 for monitoring the pressure within the system.

Other Factors for Optimizing Ozone-Mediated ODH

The productivity and selectivity of the method can be optimized. Non-limiting examples include adjusting the concentrations of components, contact time, reactant velocity, reaction temperature, or any combination thereof. Furthermore, the reactor geometry can be adjusted to maximize yields, and the reactor may include one or more materials that could play a role in radical termination, and thus affect the final product mix. In another non-limiting example, steam may be added to the reaction mixture to drive the ODH conversion forward, particularly at lower temperatures.

Abbreviations

The following abbreviations are used throughout this disclosure: BN, boron nitride; DH, dehydrogenation; F, flow rate; hBN, hexagonal form of boron nitride; ODH, oxidative dehydrogenation; ODHP, oxidative dehydrogenation of propane; P, partial pressure for a given gas; S, selectivity for a given product; % X, conversion for a given reactant.

Miscellaneous

Unless defined otherwise, all technical and scientific terms used in this disclosure, including element symbols, have the same meanings as commonly understood by one of ordinary skill in the art. Chemical compound names that are commonly used and recognized in the art are used interchangeably with the equivalent IUPAC name. For example, ethene is the same as ethylene, propene is the same as propylene, butene is the same as butylene, 2-methylpropane is the same as isobutane, and 2-methylpropene is the same as isobutene.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention is not limited to the embodiments set forth in this disclosure for illustration, but includes everything that is within the scope of the claims.

EXAMPLES

The following examples are illustrative only and do not limit the scope of the invention in any way. Indeed, various modifications of the invention in addition to those shown and described herein will become apparent to those skilled in the art from the foregoing description and the following example and fall within the scope of the appended claims.

Example 1

Oxidative Dehydrogenation of Propane to Propylene Using $O_3$ as a Mediator

In this example, proof-of-principle for using gas phase ozone ($O_3$) added to the reactant stream as a mediator for the oxidative dehydrogenation of alkanes, in the absence of a surface-based heterogeneous ODH catalyst, is shown. In the oxidative dehydrogenation of propane to propylene (ODHP), this method exhibited comparably high selectivity for the desired propylene product as previously reported for h-BN catalysts, with a maximum selectivity of greater than 80%.

Introduction

Hexagonal boron nitride and other boron-containing compositions can catalyze the selective ODH of propane to propylene. As compared to previously studied metal oxide ODH catalysts like $V/SiO_2$, these materials exhibit much higher propylene selectivity, with the major side product being ethylene and not CO and $CO_2$ ($CO_x$). The differences in reactivity between boron-containing materials and metal oxides has spurred our further studies into the reaction kinetics in order to determine the mechanism of increased selectivity of ODH using these materials as catalysts.

Studies have shown that the oxidation of alkanes over these materials proceeds through a surface-mediated gas-phase reaction, where reactive surface $BO_x$ species abstract H from propane to form propyl radicals that react further gas phase with $O_2$ to provide the high olefin selectivity exhibited by boron-based catalysts.

Summary

In this example, a selective oxidation is performed with trace amounts of gaseous $O_3$ within the feed in the absence of a catalyst. The $O_3$ acts as a gas phase initiator, decomposing to form $O_2$ and the O• radical.

As shown in this example, ozone added to the reactant stream can be used as a mediator in a solely homogeneous gas-phase reactive pathway, with very high selectivity for the desired product. No heterogeneous catalyst or catalytic surface is needed to obtain these results, thus removing the complications and expense of catalyst development, synthesis, and/or replacement.

Methods, Results and Discussion.

The experimental setup used to generate and to use $O_3$ as an ODHP mediator is illustrated in FIG. 1. Ozone is generated within the $O_3$ generator 14 from oxygen in the air or pure oxygen 20 that is fed into the $O_3$ generator. The ozone is fed into a reactant stream that further includes propane 16 and oxygen from the air 18. Diluents of the reactant stream, such as $N_2$ from a nitrogen source 22 and inert gases from a tank 24 are added to obtain the desired reactor concentrations of propane and oxygen. Note that the $O_3$ generator can produce variable amounts of $O_3$ by adjusting the generator settings. However, in these experiments, $O_3$ generation was set at a constant rate, and the desired $O_3$ concentration was obtained through the appropriate dilution with the various components of the reaction mixture.

The reaction mixture containing oxygen, propane, ozone and other components is sent through the reactor 12 at the desired rate of flow and at the desired temperature. The reaction mixture reacts within the reactor 12, and the resulting reactor effluent is analyzed by a gas chromatograph 28, to determine the identity and amount of product(s) formed.

Flow rates of propane (instrument grade, Matheson), oxygen (UHP, Airgas), and nitrogen (UHP, Airgas) were controlled using three mass flow controllers (Bronkhorst) calibrated to each individual gas to allow total flowrates of 40-200 mL min$^{-1}$. The reactor effluent was passed through a thermoelectrically-cooled liquid-gas separator to condense formed water before being analyzed by an Inficon Micro GC Fusion equipped with three columns (Rt-Molsieve 5a, Rt-U Bond, and Rt-Alumina Bond/Na$_2$SO$_4$) with individual thermal conductivity detectors (TCD). The carbon balance of each data point closes within 5%.

Equations:
Alkane Conversion, X (%)

$$X = \frac{\sum F_{carbon\ out}}{F_{alkane\ in}} * 100\%$$

where $F_{carbon\ out}$=of all carbon products from reactor in mol s$^{-1}$ and $F_{alkane\ in}$ flow of all alkane into reactor in mol s$^{-1}$
Product Selectivity, S (%)

$$S = \frac{F_{product\ out}}{\sum F_{carbon\ out}} * 100\%$$

where $F_{product\ out}$=flow of product from reactor in mol s$^{-1}$ and $F_{carbon\ out}$=flow of all carbon products from reactor in mol s$^{-1}$
Inverse weight-hour-space-velocity, WHSV$^{-1}$ (kg$_{cat}$ s mol$_{alkane}^{-1}$)

$$WHSV^{-1} = \frac{M_{cat} * (V/n)_{STP}}{F_{total} * N_{C3H8}}$$

where M$_{cat}$=mass of catalyst loaded in reactor (kg), (V/n)$_{STP}$=24.5 (L/mol) at 298.15 K, (1 atm, R=8.206*10$^{-2}$ L atm K$^{-1}$ mol$^{-1}$), F$_{tot}$=total flow of all inlet gases (L s$^{-1}$), and N$_{alkane}$=mol percent alkane in gas feed (mol %).

Figure 2:
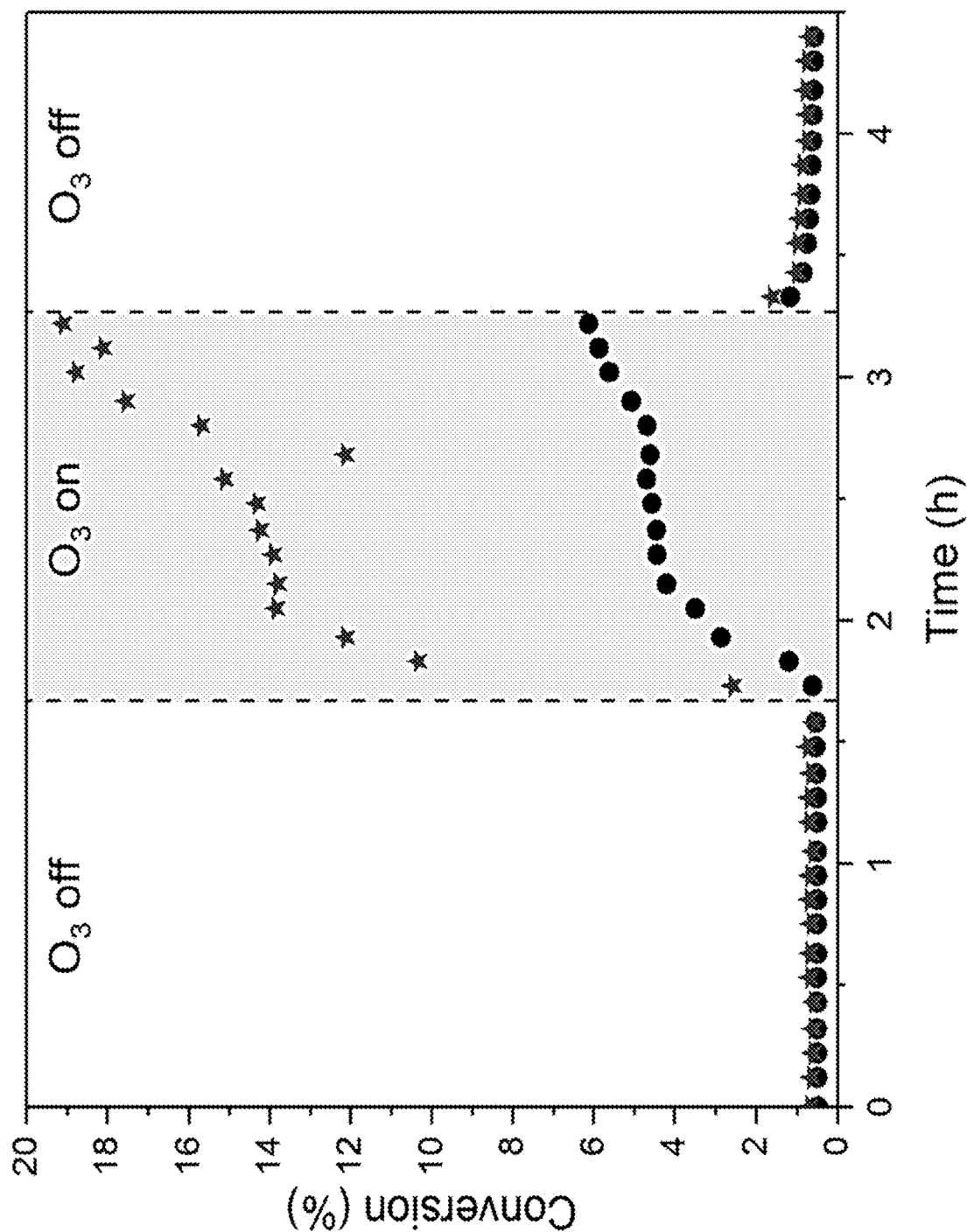
FIG. 2 is a graph illustrating % conversion of propane as a function of time through a time period of no $O_3$ exposure, a subsequent time period of $O_3$ exposure, and a final time period of no $O_3$ exposure. Propylene was the major product of propane conversion.

In an initial experiment, a typical reaction mixture of 30% C$_3$H$_8$ (P$_{C3H8}$=0.30 atm), 15% O$_2$ (P$_{O2}$=0.15 atm) and 55% N$_2$ (P$_{N2}$=0.55 atm) was sent through the reactor at a flow rate (F$_{tot}$) of 80 mL/min and at a temperature (T) of 450° C. In an initial 1.7 h time block, no ozone was added to the mixture, and only minimal background conversion was observed (FIG. 2, left third). For the next 1.6 h, the 15% O$_2$ was replaced with O$_2$ passed through the ozone generator, resulting in ~1000 ppm O$_3$ and 14.9% O$_2$. During this time period, significant conversion of propane to propylene was observed (FIG. 2, center third). Subsequently, the feed from the ozone generator was stopped and replaced with 15% oxygen, resulting in a drop in propane conversion back to the minimal background levels (FIG. 2, right third). These results demonstrate that ozone is an effective mediator for gas phase ODHP, even in the absence of an ODH catalyst.

Figure 3:
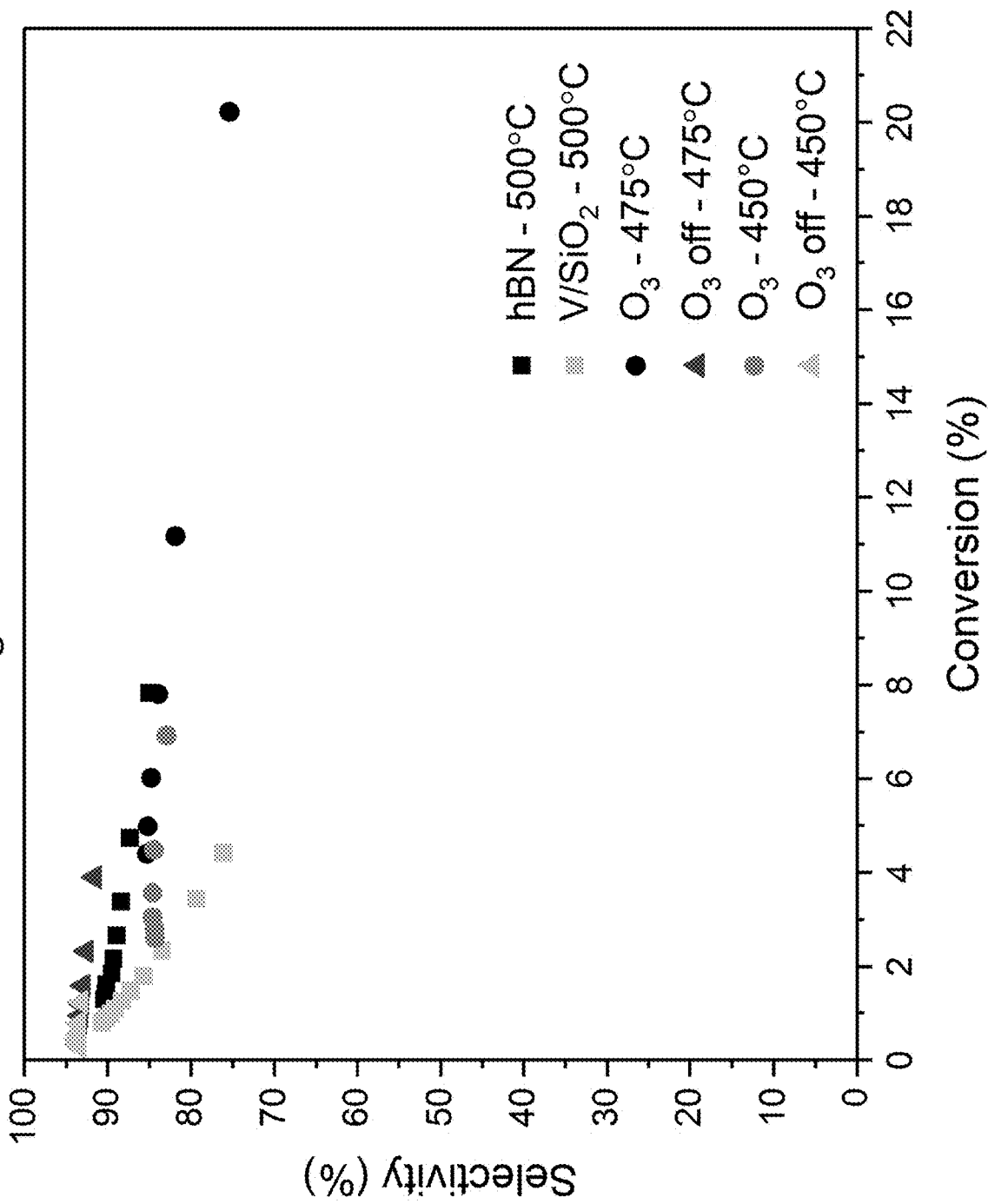
FIG. 3 is a graph illustrating propylene selectivity as a function of % conversion for $O_3$-mediated ODHP, hBN-catalyzed ODHP, and $V/SiO_2$-catalyzed ODHP. $O_3$-mediated ODHP conditions: $P_{C3H8}$=0.30 atm, $P_{O2}$=0.149 atm, $P_{N2}$=0.55 atm, 730 ppm $O_3$. hBN- and $V/SiO_2$-catalyzed conditions: $P_{C3H8}$=0.30 atm, $P_{O2}$=0.15 atm, $P_{N2}$=0.55 atm.

We then collected propylene selectivity, % conversion, and product distribution data using a reactant stream made up of 30% C$_3$H$_8$ (P$_{C3H8}$=0.30 atm), ~15% O$_2$ (P$_{O2}$=0.15 atm) and 55% N$_2$ (P$_{N2}$=0.55 atm), both with and without added O$_3$ (730 ppm) and at two different temperatures (T=450° C. and 475° C.). FIG. 3 shows the influence of C$_3$H$_8$ conversion on the C$_3$H$_6$ selectivity of the O$_3$-mediated ODH in the empty reactor (heated zone: 76.3 cm$^3$), as compared to hBN- and V/SiO$_2$-catalyzed ODH in filled reactors at 500° C. (F$_{tot}$=40-140 mL/min in the various setups).

As seen in FIG. 3, under the given conditions, conversion of C$_3$H$_8$ in the empty reactor is limited without O$_3$ present. The introduction of 730 ppm of O$_3$ substantially increases the conversion of C$_3$H$_8$ with high selectivity at both 450° C. and 475° C. Notably, the high selectivity is maintained at higher propane conversions. The large increase in conversion seen upon introduction of trace amounts of O$_3$ suggests that O$_3$ acts as a catalyst rather than as a stoichiometric reactant in the transformation of C$_3$H$_8$ to olefins and other products. Furthermore, the similar selectivity observed in the transformation of C$_3$H$_8$ in the presence of O$_3$/O$_2$ as compared to hBN-catalyzed ODH suggests that similar reactive pathways are accessed in both systems.

Figure 4:
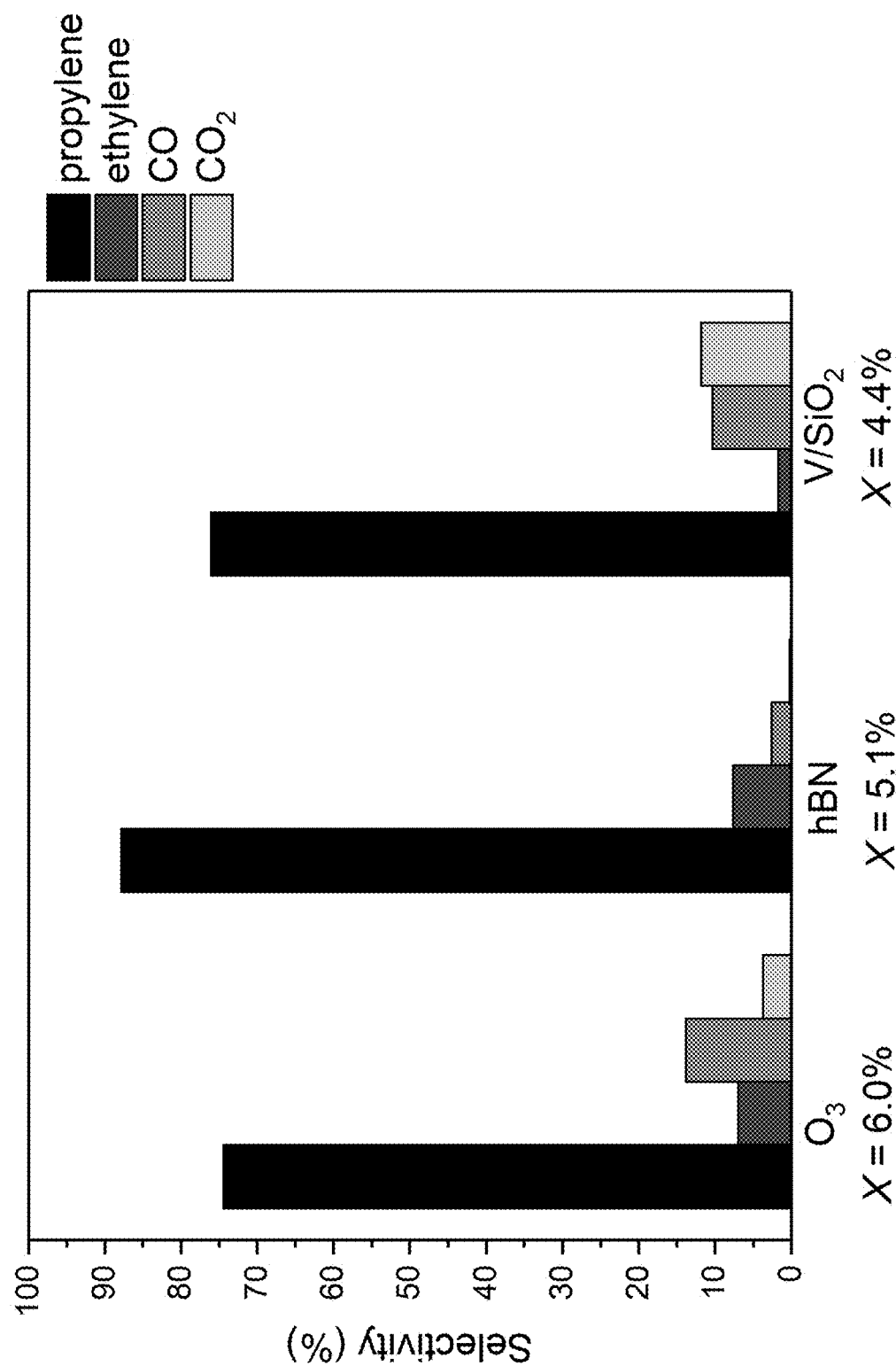
FIG. 4 is a bar graph illustrating the resulting product distribution of ODHP mediated by $O_3$, $O_3$-mediated ODHP conditions: $P_{C3H8}$=0.30 atm, $P_{O2}$=0.149 atm, $P_{N2}$=0.55 atm, 730 ppm $O_3$.

FIG. 4 shows the product distribution at similar levels of C$_3$H$_8$ conversion using O$_3$, hBN, and V/SiO$_2$. O$_3$ and hBN demonstrate similar product distributions, further reflecting similarities in reaction mechanism. Compared to the traditional metal oxide system V/SiO$_2$, O$_3$ demonstrates significantly higher selectivity to light olefins.

Figure 5:
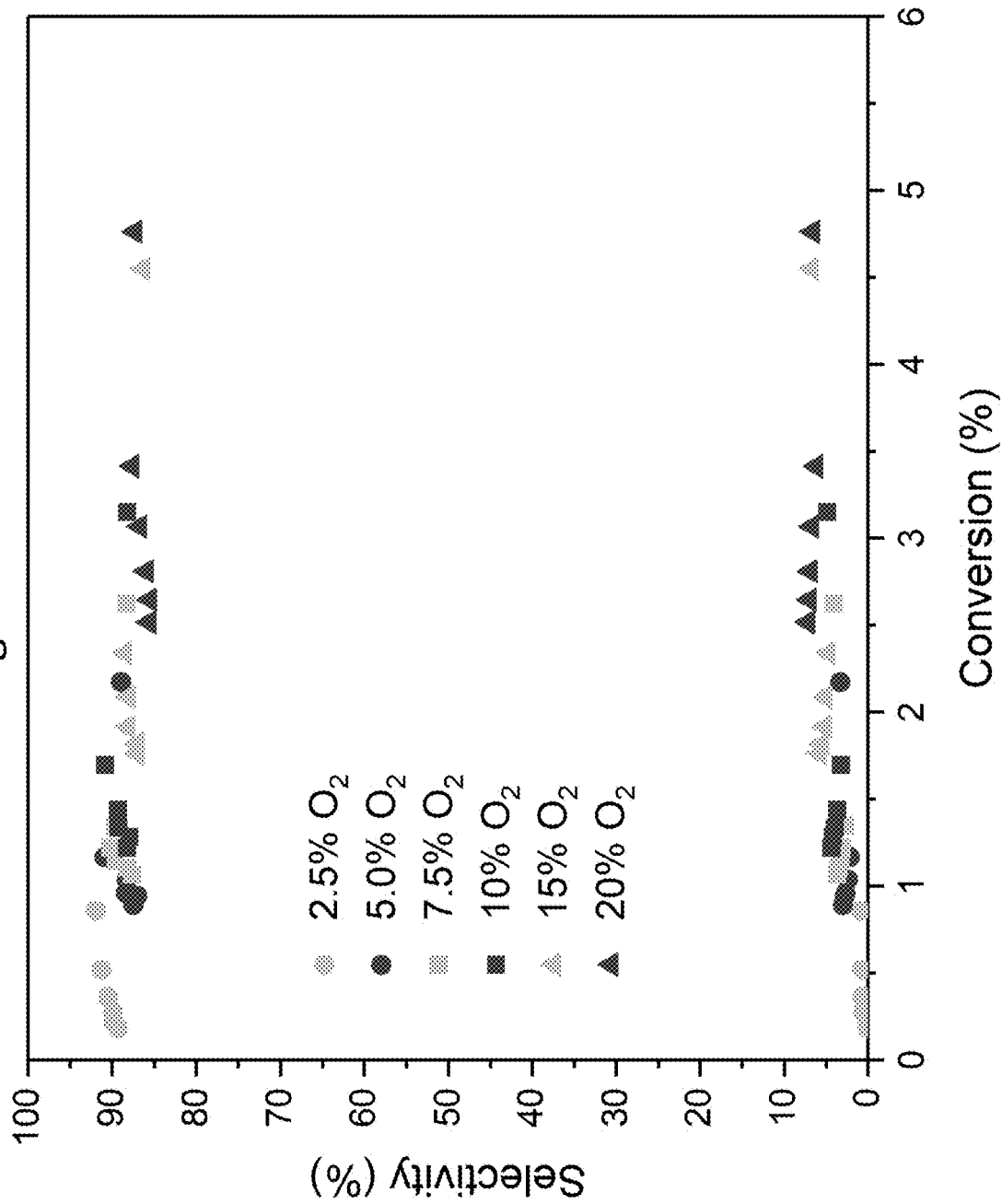
FIG. 5 is a graph illustrating propylene selectivity as a function of % conversion for $O_3$-mediated ODHP at variable concentrations of $O_2$ and constant $O_3$. $P_{C3H8}$=0.30 atm, 120 ppm $O_3$, $O_2$ concentration indicated, balance $N_2$. $F_{tot}$=40-140 mL min$^{-1}$. T=450°.

To begin to determine parameters for optimal selectivity, we next collected propylene and CO selectivity and % conversion data using reactant streams made up of 30% C$_3$H$_8$ (P$_{C3H8}$=0.30 atm), constant added O$_3$ (120 ppm), variable concentrations of O$_2$ (2.5%, 5.0%, 7.5%, 10%, 15% and 20%) and the balance N$_2$ at T=450° C. (F$_{tot}$=40-140 mL/min). FIG. 5 shows the selectivity trend of O$_3$-mediated ODH at varying concentrations of O$_2$. As the O$_2$ concentration increases, propylene selectivity decreases and CO selectivity increases. Therefore, lower O$_2$ concentrations are required to enhance propylene selectivity.

Figure 6:
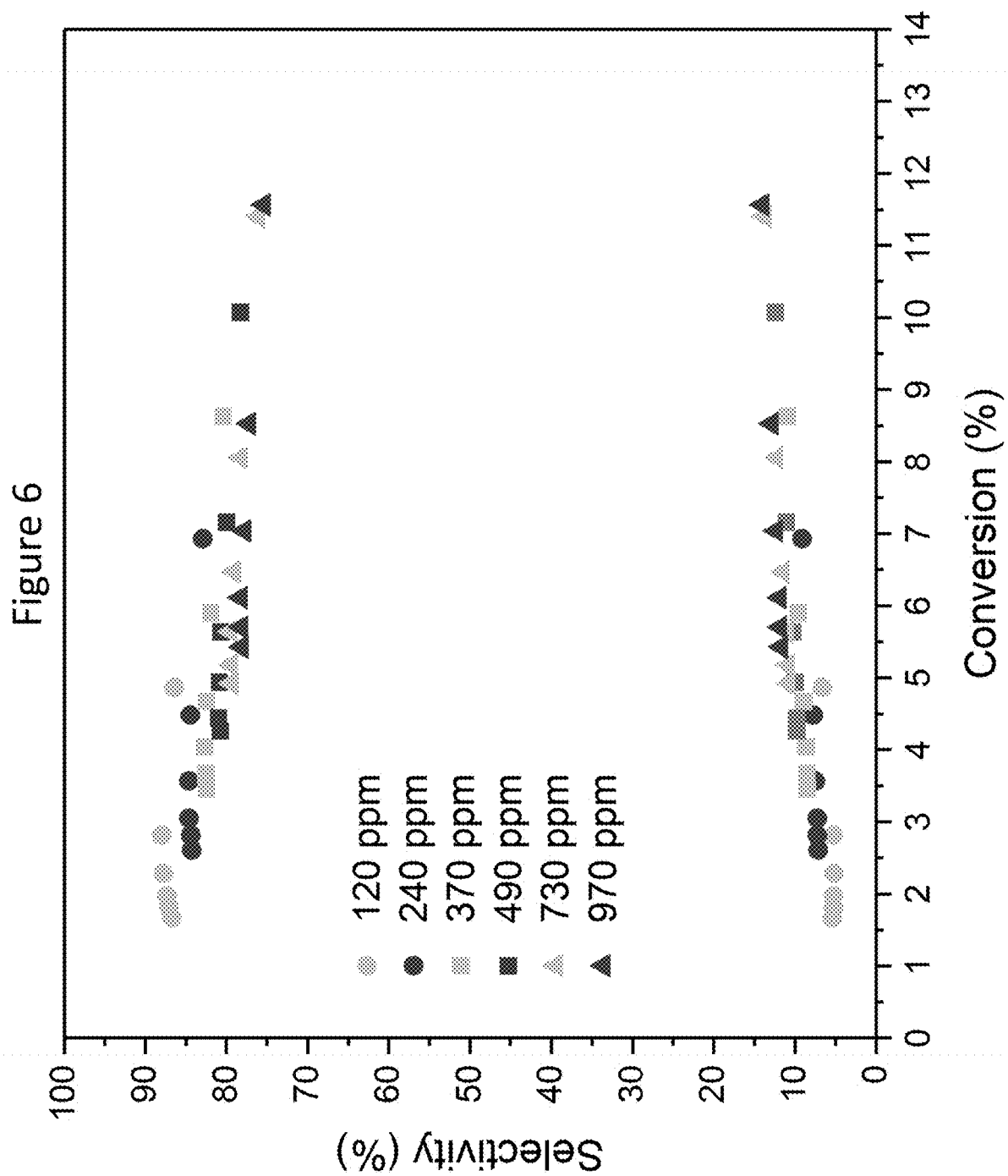
FIG. 6 is a graph illustrating propylene selectivity as a function of % conversion for $O_3$-mediated ODHP at variable concentrations of $O_3$ and constant $O_2$. $P_{C3H8}$=0.30 atm, $P_{O2}$=0.15 atm, $O_3$ concentration indicated, balance $N_2$. $F_{tot}$=40-140 mL min$^{-1}$. T=450° C.
Figure 7:
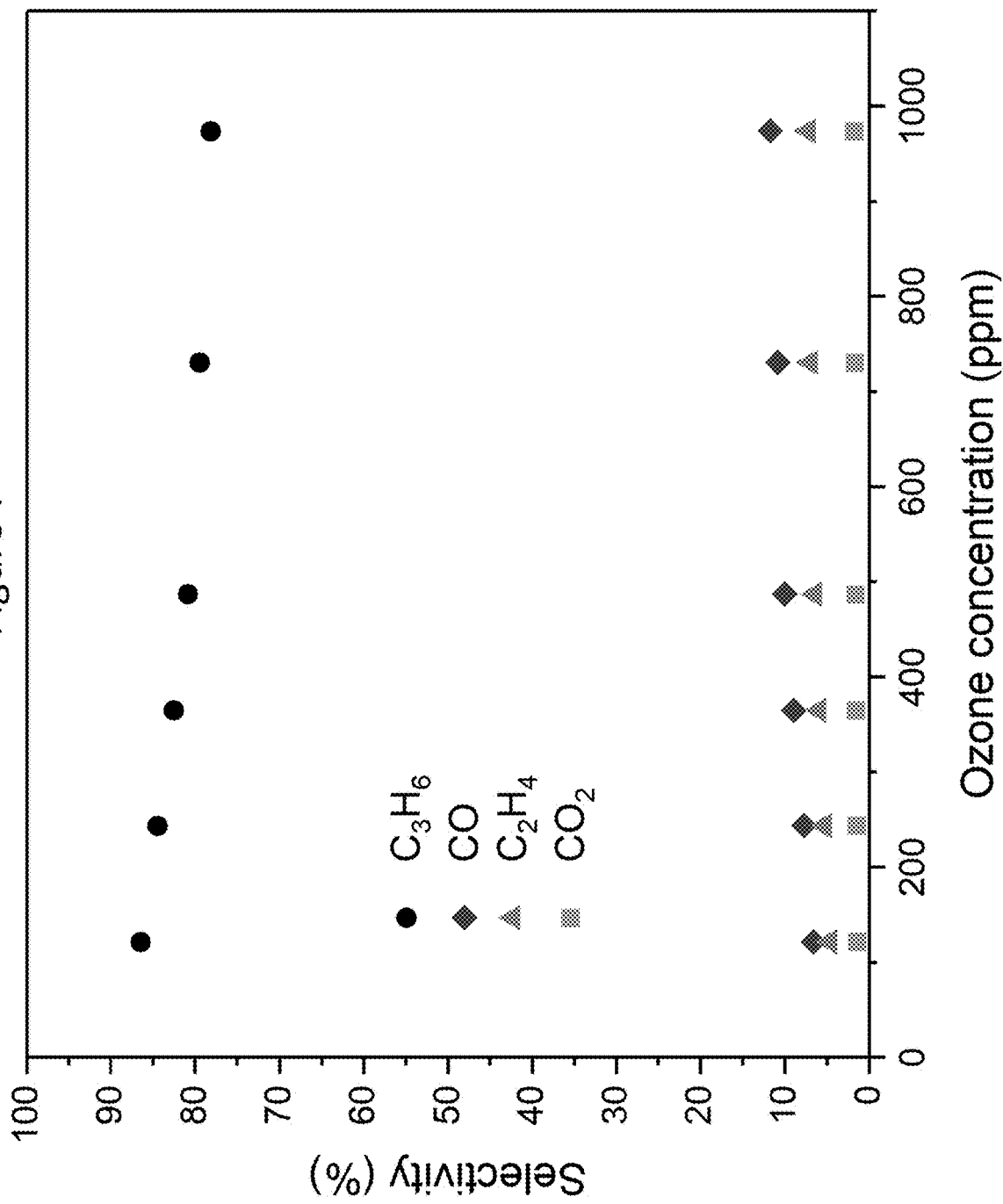
FIG. 7 is a graph illustrating propylene selectivity as a function of $O_3$ concentration for $O_3$-mediated ODHP at $X_{C3H8}$=4.5-5.4%. $P_{C3H8}$=0.30 atm, $P_{O2}$=0.15 atm, $O_3$ concentration indicated, balance $N_2$. $F_{tot}$=40-140 mL min$^{-1}$. T=450° C.

To continue to explore parameters for optimal selectivity, we next collected propylene and CO selectivity and % conversion data using reactant streams made up of 30% C$_3$H$_8$ (P$_{C3H8}$=0.30 atm), variable added O$_3$ (120 ppm, 240 ppm, 370 ppm, 490 ppm, 730 ppm and 970 ppm), a constant concentration of O$_2$ (15%) and the balance N$_2$ at T=450° C. (F$_{tot}$=40-140 mL/min). FIG. 6 shows the selectivity trend of O$_3$-mediated ODH at variable concentrations of O$_3$. As the amount of O$_3$ in the feed increases, propylene selectivity decreases with a concurrent increase in CO selectivity. FIG. 7 shows the product selectivity at isoconversion (4.5-5.4% conversion) as a function of O$_3$ concentrations. Lower concentrations of O$_3$ enhance the overall selectivity to the desired propylene product. Without being bound by any theory, increasing O$_3$ may lead to ozonolysis, which can decompose into CO/CO$_2$.

In sum, these experiments demonstrate that optimal propylene selectivity is obtained at lower O$_2$ and O$_3$ concentrations, while increased activity is observed with higher O$_2$ and O$_3$ concentrations.

Figure 8:
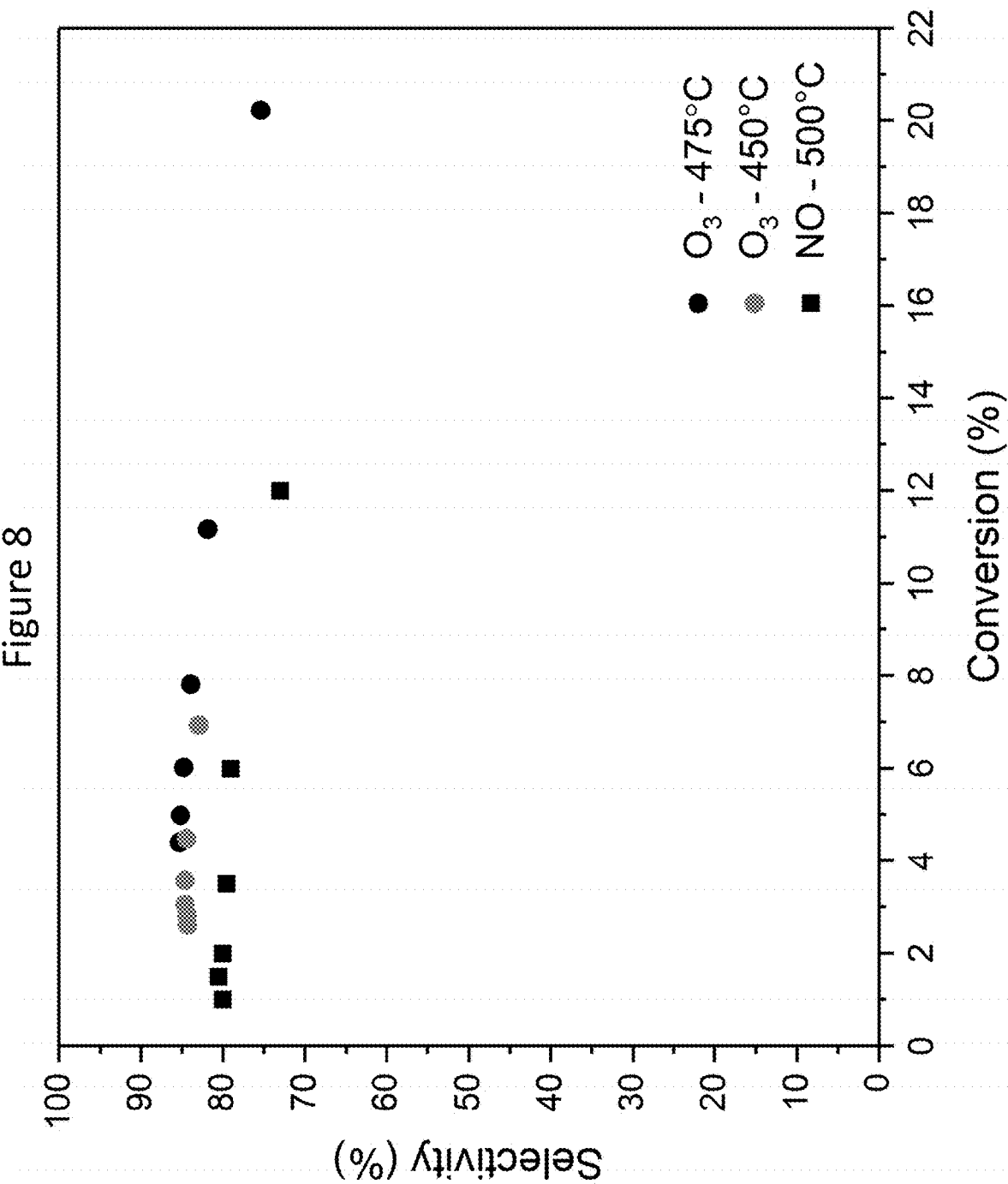
FIG. 8 is a graph illustrating propylene selectivity as a function of % conversion for both $O_3$ and NO-mediated ODHP systems. $O_3$ conditions: $P_{C3H8}$=0.30 atm, 120 ppm $O_3$, $P_{O2}$=0.15 atm, balance $N_2$. $F_{tot}$=40-140 mL min$^{-1}$. NO conditions: $P_{C3H8}$=0.03 atm, $P_{O2}$=0.10 atm, $P_{NO}$=0.005 atm, balance He.

Next, we compared our results (P$_{C3H8}$=0.30 atm; P$_{O2}$=~0.15 atm; P$_{N2}$=0.55 atm; 730 ppm O$_3$; T=450° C. and 475° C.; F$_{tot}$=40-140 mL/min) to results reported for NO-mediated ODHP (Annamalai, L., et al., *ACS Catalysis* 2019 9 (11), 10324-10338; P$_{C3H8}$=0.03 atm; P$_{O2}$=0.10 atm; P$_{NO}$=0.005 atm; balance He). FIG. 8 shows the comparison in selectivity between O$_3$- and NO-mediated ODH. O$_3$-mediated ODH showed higher selectivity than NO-mediated ODH. One of the disadvantages of the NO system includes the formation of corrosive $HNO_3$, which would greatly hamper industrial implementation.

Figure 9:
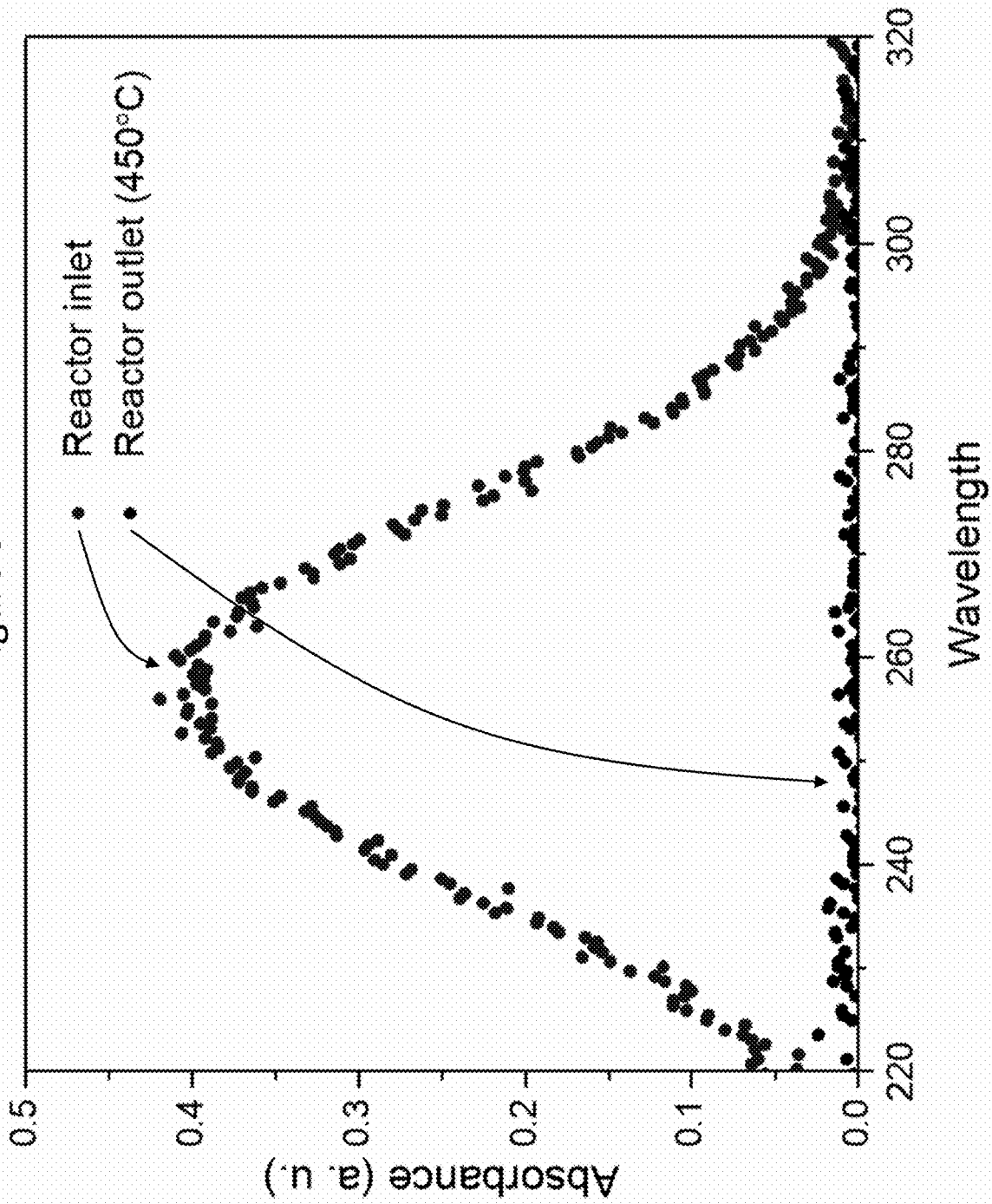
FIG. 9 is a graph illustrating the consumption of all $O_3$ within the reactor for $O_3$-mediated ODHP at 450° C.

For safety reasons, it is important that no $O_3$ remain in the reactor effluent containing the ODH product(s). To confirm that our method passes this test, we tested the reactor flow for the reaction at 450° C. for the presence of $O_3$ at both the reactor inlet and the reactor outlet (containing the effluent). As seen in FIG. 9 (and as expected/required), the inlet reactant stream exhibited the absorbance peak indicating the presence of $O_3$, However, the outlet effluent contained no $O_3$ (FIG. 9). Thus, in this setup, all the $O_3$ was consumed within reactor, alleviating any potential safety concerns.

Conclusion.

In sum, this example demonstrates that ozone added to the reactant stream can be used as an ODH mediator in a solely homogeneous gas-phase reactive pathway, with very high selectivity for the desired product. Because no heterogeneous catalyst or catalytic surface is needed to obtain these results, this method could be applied to create an efficient and cost-effective process for the commercial production of light olefins from a light alkane-containing feedstock, requiring (in addition to the light alkane) only ozone (which can be continuously generated on-site) and oxygen from ambient air.

Example 2

Oxidative Dehydrogenation of Propane to Propylene Using $O_3$ as a Mediator

The experimental setup used to generate and to use $O_3$ as an ODHP mediator is illustrated in FIG. 1. Ozone is generated within the $O_3$ generator 14 from oxygen 20 that is fed into the $O_3$ generator. The ozone is fed into a reactant stream that further includes propane 16 and oxygen from the air 18. Diluents of the reactant stream, such as $N_2$ from a nitrogen source 22 and inert gases from a tank 24 are added to obtain the desired reactor concentrations of propane and oxygen. Water is fed via a syringe pump and evaporated at 120° C. upstream of the reactor inlet. Note that the $O_3$ generator can produce variable amounts of $O_3$ by adjusting the generator settings. However, in these experiments, $O_3$ generation was set at a constant rate, and the desired $O_3$ concentration was obtained through the appropriate dilution with the various components of the reaction mixture.

The reaction mixture containing oxygen, propane, ozone and other components is sent through the reactor 12 at the desired rate of flow and at the desired temperature. The reaction mixture reacts within the reactor 12, and the resulting reactor effluent is analyzed by a gas chromatograph 28, to determine the identity and amount of product(s) formed.

Flow rates of propane (instrument grade, Matheson), and nitrogen (UHP, Airgas) were controlled using three mass flow controllers (Bronkhorst) calibrated to each individual gas to allow total flowrates of 40-120 mL min$^{-1}$. The reactor effluent was passed through a thermoelectrically-cooled liquid-gas separator to condense formed water before being analyzed by an Inficon Micro GC Fusion equipped with three columns (Rt-Molsieve 5a, Rt-U Bond, and Rt-Alumina Bond/$Na_2SO_4$) with individual thermal conductivity detectors (TCD). The carbon balance of each data point closes within 5%.

Equations:
Alkane Conversion, X (%)

$$X = \frac{\sum F_{carbon\ out}}{F_{alkane\ in}} * 100\%$$

where $F_{carbon\ out}$=of all carbon products from reactor in mol s$^{-1}$ and $F_{alkane\ in}$ flow of all alkane into reactor in mol s$^{-1}$
Product Selectivity, S (%)

$$S = \frac{F_{product\ out}}{\sum F_{carbon\ out}} * 100\%$$

where $F_{product\ out}$=flow of product from reactor in mol s$^{-1}$ and $F_{carbon\ out}$=flow of all carbon products from reactor in mol s$^-$
Contact Time, CT (min)

$$CT = \frac{V_{reactor}}{F_{total}}$$

where $V_{reactor}$=reactor volume (mL) and $F_{tot}$=total flow of all inlet gases (mL/min).

Figure 10:
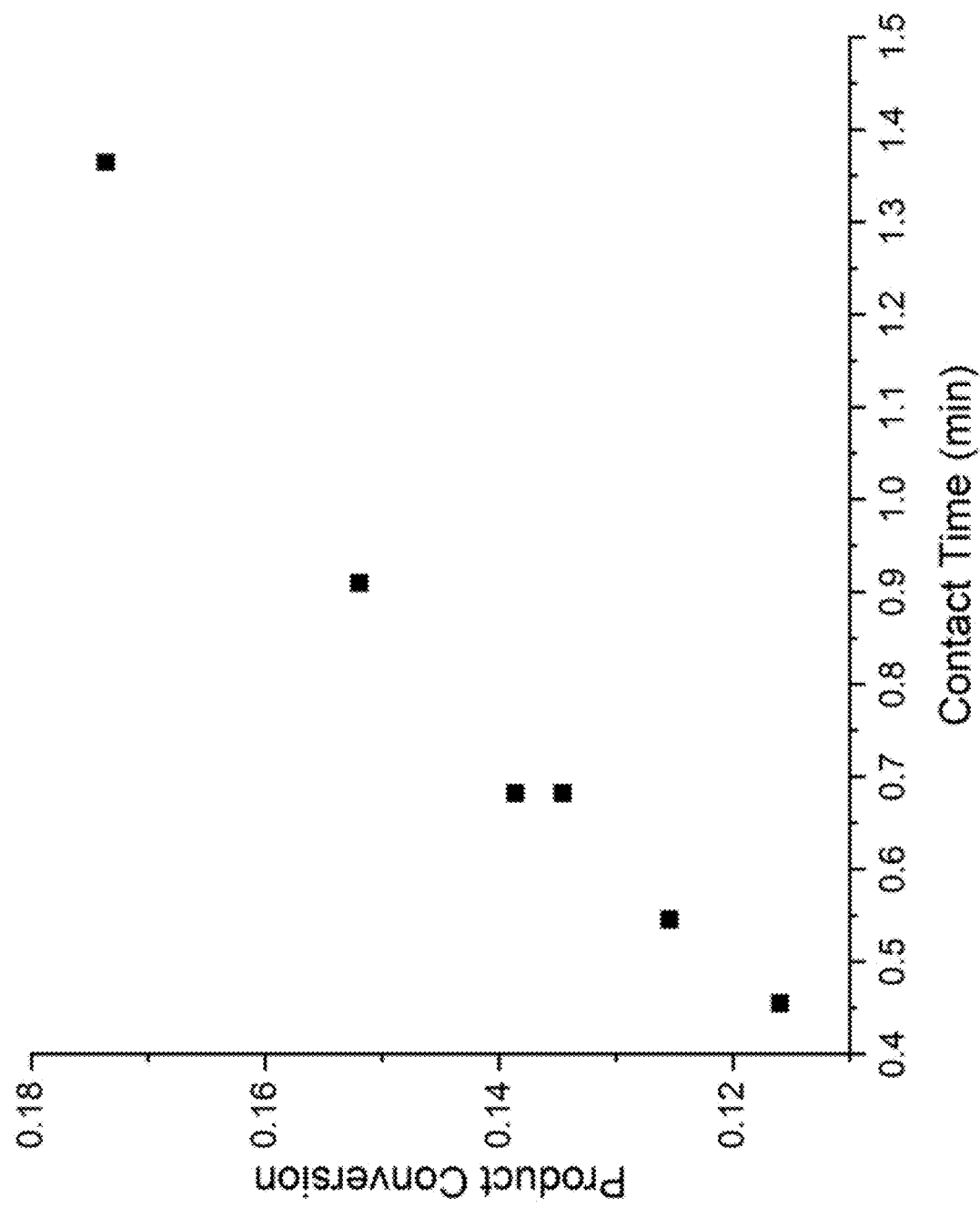
FIG. 10 is a graph illustrating propane conversion as a function of contact time. Conditions: 500° C., 40-120 mL/min total flow, $P_{C3H8}$=0.30 atm, <1000 ppm $O_3$, $P_{O2}$=0.15 atm, balance $N_2$.
Figure 11:
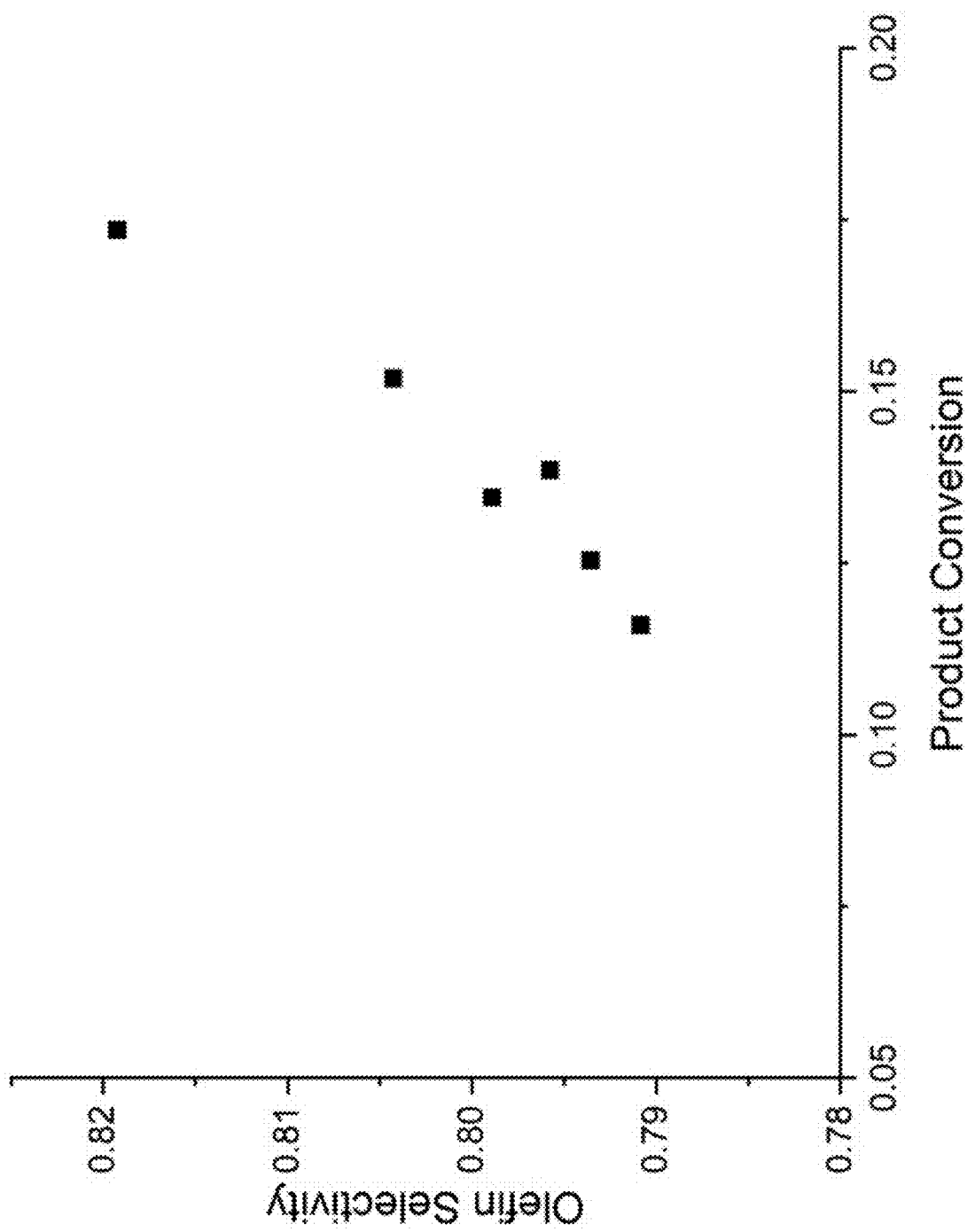
FIG. 11 is a graph illustrating product olefin selectivity as a function of propane conversion. Conditions: 500° C., 40-120 mL/min total flow, $P_{C3H8}$=0.30 atm, <1000 ppm $O_3$, $P_{O2}$=0.15 atm, balance $N_2$.

In a follow-up experiment, a typical reaction mixture of 30% $C_3H_8$ ($P_{C3H8}$=0.30 atm), 15% $O_2$ ($P_{O2}$=0.15 atm), <1000 ppm $O_3$, and balance $N_2$ ($P_{N2}$≈0.55 atm) was sent through the reactor at a flow rate ($F_{tot}$) of 40-120 mL/min and at a temperature (T) of 500° C. The experiment demonstrated an increase in product conversion with contact time (FIG. 10) and an increase in product selectivity with product conversion (FIG. 11). Surprisingly, both conversion and selectivity increased. Typically, selectivity decreases with increasing conversion. This demonstrates that at elevated temperatures $O_3$-mediated ODH exhibits exceptional selectivity to olefin products even with extended contact time.

Figure 12:
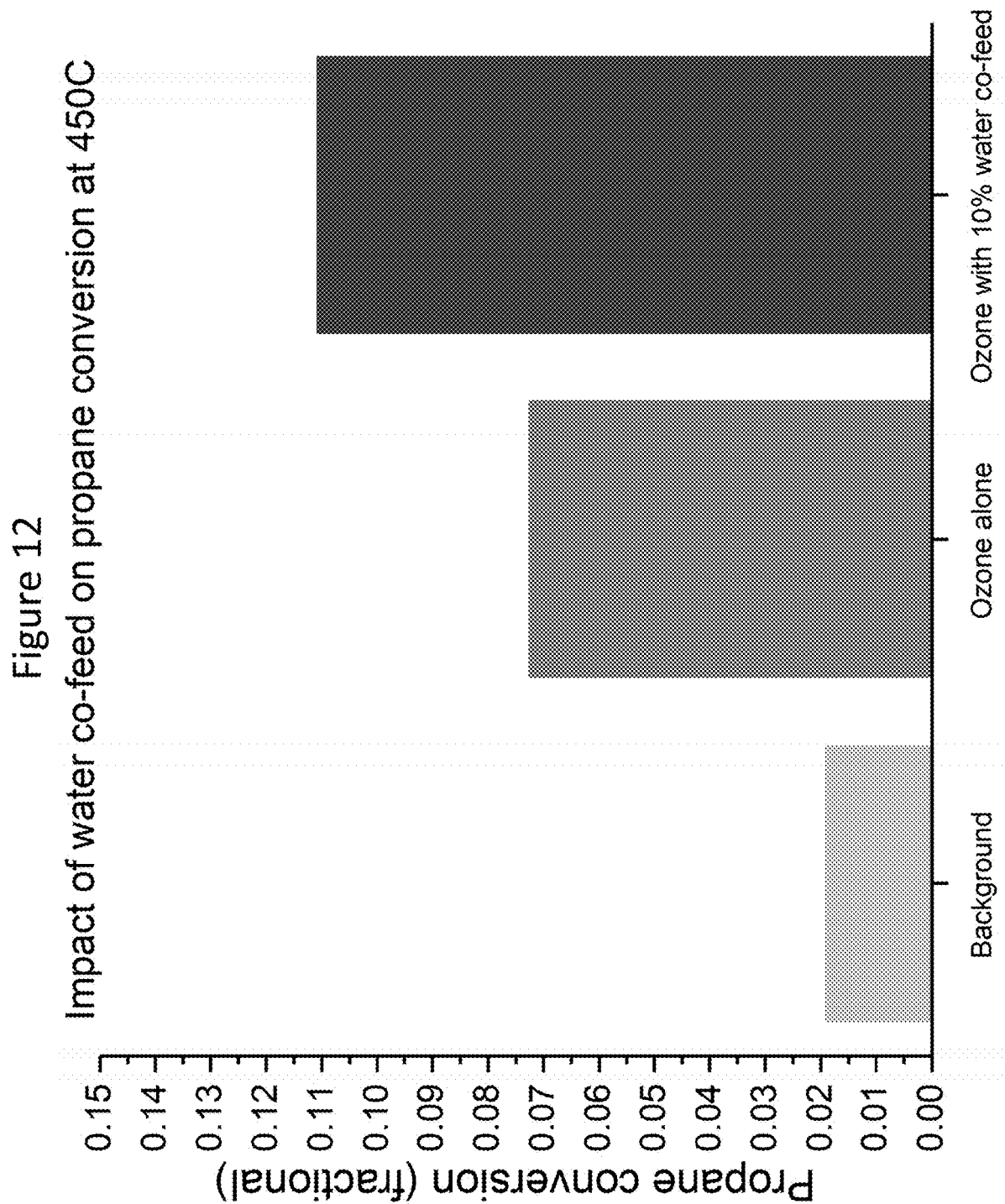
FIG. 12 is a graph illustrating propane conversion in the presence of $O_3$, $O_3$ and $H_2O$, and just $H_2O$. Conditions: 450° C., 80 mL total flow rate, $P_{C4H10}$=0.30 atm, <1000 ppm $O_3$, $P_{O2}$=0.15 atm, $P_{H2O}$=0.10 atm, balance $N_2$.
Figure 13:
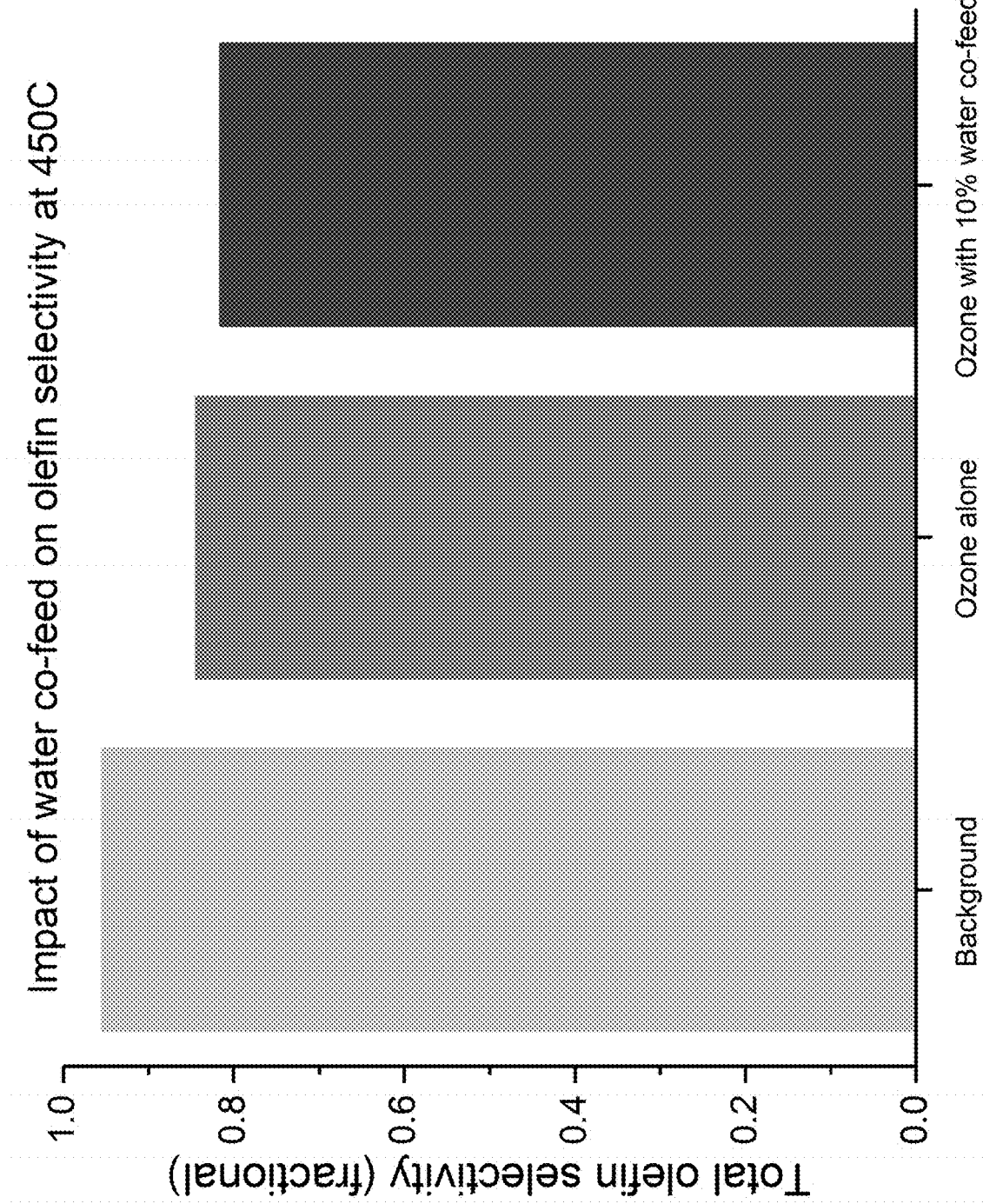
FIG. 13 is a graph illustrating propane conversion in the presence of $O_3$, $O_3$ and $H_2O$, and just $H_2O$. Conditions: 450° C., 80 mL total flow rate, $P_{C4H10}$=0.30 atm, <1000 ppm $O_3$, $P_{O2}$=0.15 atm, $P_{H2O}$=0.10 atm, balance $N_2$.

In a further experiment, a typical reaction mixture of 30% $C_3H_8$ ($P_{C3H8}$=0.30 atm), 15% $O_2$ ($P_{O2}$=0.15 atm), <1000 ppm $O_3$, 10% $H_2O$, ($P_{H2O}$=0.10 atm) and balance $N_2$ ($P_{N2}$≈0.45 atm) was sent through the reactor at a flow rate ($F_{tot}$) of 80 mL/min and at a temperature (T) of 450° C. The experiment demonstrated an increase in product conversion (FIG. 12) by substituting a portion of the $N_2$ diluent for $H_2O$. This demonstrates that steam serves as an effective diluent for $O_3$-mediated ODH and plays a role enhancing conversion without substantially reducing selectivity (FIG. 13).

We claim:
1. A method of making one or more desired chemical products comprising contacting one or more liquid or gaseous reactants with oxygen ($O_2$) and ozone ($O_3$), whereby the ozone mediates the oxidative dehydrogenation (ODH) of the one or more liquid or gaseous reactants to form the one or more desired chemical products,
    wherein the one or more liquid or gaseous reactants comprises an alkane or a hydrocarbon comprising an alkyl group and the desired chemical products comprise one or more olefins or one or more hydrocarbons comprising an alkenyl group, and
    wherein the contacting step occurs in the absence of a heterogeneous ODH catalyst or a catalytically active surface.

2. The method of claim 1, wherein the one or more liquid or gaseous reactants are selected from a $C_2$-$C_5$ n-alkane, a $C_3$-$C_5$ iso-alkane, a $C_2$-$C_5$ alkylbenzene, and any combination thereof.

3. The method of claim 1, wherein the one or more liquid or gaseous reactants comprises butane and the desired chemical product comprises 1-butene, 2-butene, isobutene, butadiene, or any combination thereof or wherein the one or more liquid or gaseous reactants comprises propane and the desired chemical product is propene.

4. The method of claim 1, wherein the contacting step occurs within a reactor chamber wherein one or more optional diluents are introduced into the reactor chamber, and the ozone is introduced into the reactor chamber at a concentration from 0.1 to 1000 ppm, based on the total volume of the one or more liquid or gaseous reactants, the oxygen, the ozone, and the one or more optional diluents.

5. The method of claim 4, wherein the temperature within the reactor chamber is from 400° C. to 800° C.

6. The method of claim 4, wherein the oxygen is introduced into the reactor chamber at a concentration from 1% to 25% by volume, based on the total volume of the one or more liquid or gaseous reactants, the oxygen, the ozone, and the one or more optional diluents.

7. The method of claim 4, wherein the one or more liquid or gaseous reactants are introduced into the reactor chamber at a concentration from 5% to 50% by volume, based on the total volume of the one or more liquid or gaseous reactants, the oxygen, the ozone, and the one or more optional diluents.

8. The method of claim 4, wherein the oxygen, the ozone, and the one or more liquid or gaseous reactants are introduced into the reactor chamber together.

9. The method of claim 4, wherein the reactor chamber comprises one or more inlets dispersed along the chamber to introduce the oxygen or the ozone into a reaction path for a propagating reactant stream of the one or more liquid or gaseous reactants through the reactor chamber.

10. The method of claim 4, wherein the reactor chamber does not include a heterogeneous ODH catalyst or a catalytically active surface.

11. The method of claim 4, wherein the one or more optional diluents are selected from nitrogen ($N_2$), water ($H_2O$), methane ($CH_4$), and carbon dioxide ($CO_2$), and are introduced into the reactor chamber.

12. The method of claim 11, wherein nitrogen is introduced into the reactor chamber at a concentration from 0.01% to 70% by volume, based on the total volume of the one or more liquid or gaseous reactants, the oxygen, the ozone, and the one or more diluents.

13. The method of claim 4, wherein the oxygen is introduced into the reactor chamber at a concentration from 1% to 25% by volume, based on the total volume of the one or more liquid or gaseous reactants, the oxygen, the ozone, and the one or more optional diluents; the one or more liquid or gaseous reactants are introduced into the reactor chamber at a concentration from 5% to 50% by volume, based on the total volume of the one or more liquid or gaseous reactants, the oxygen, the ozone, and the one or more optional diluents; and the temperature within the reactor chamber is from 400° C. to 800° C.

14. The method of claim 1, wherein the method exhibits greater than 70% selectivity for the desired chemical products comprising one or more olefins or one or more hydrocarbons comprising an alkenyl group.

15. The method of claim 1, wherein the one or more liquid or gaseous reactants are further contacted with steam.

* * * * *